# United States Patent [19]

Jackson et al.

[11] 4,256,838

[45] Mar. 17, 1981

[54] METHOD OF PURIFICATION OF GLUCOSE ISOMERASE

[75] Inventors: Denise M. Jackson, Chicago; Yoshihisa Tsuda, Highland Park; Vida Winans, Downers Grove, all of Ill.

[73] Assignee: UOP Inc., Des Plaines, Ill.

[21] Appl. No.: 93,569

[22] Filed: Nov. 13, 1979

[51] Int. Cl.³ .............................................. C12N 9/92
[52] U.S. Cl. .................................. 435/234; 435/814; 435/815; 435/827; 435/853; 435/886
[58] Field of Search ................ 435/233, 234, 814, 815

[56] References Cited

U.S. PATENT DOCUMENTS 4,077,842  3/1978  Cory ..................................... 435/188

OTHER PUBLICATIONS

Palleroni et al., "Mannose Isomerase of Pseudomonas Saccharophila", Journal of Biological Chemistry, 1956, vol. 218, pp. 535-548.

Yamanaka, "D-Xylose Isomerase", Methods in Enzymology, vol. IX, pp. 588-593, (1966).

Takasaki et al., "Studies on Sugar Isomerizing Enzyme", Agr. Biol. Chem., vol. 33, No. 11, pp. 1527-1534, (1969).

*Primary Examiner*—Lionel M. Shapiro
*Attorney, Agent, or Firm*—James R. Hoatson, Jr.; Raymond H. Nelson; William H. Page, II

[57] ABSTRACT

A process for purifying an enzyme such as glucose isomerase which comprises precipitating nucleic acids from a cell-free, heat-treated enzyme solution in a suitable buffer and chromatographing the supernatant on a cellulosic medium. Subsequent chromatography on a hydrophilic, molecular-sieve medium affords enzyme of about 90% purity.

8 Claims, No Drawings

METHOD OF PURIFICATION OF GLUCOSE ISOMERASE

BACKGROUND OF THE INVENTION

It is known that fructose is substantially sweeter than glucose. Because the latter is relatively inexpensive and readily available, it is desirable to have an efficient and economical means of converting glucose to fructose. The alkali isomerization of glucose yields fructose, but the production of undesirable side products and the necessity of removing caustic and other materials from a food ingredient make this route unattractive. A preferred method of isomerization utilizing enzymes has the advantages of specificity of reactions and lesser likelihood of producing undesirable side products which must be removed before the fructose-containing material can be used in foods. The enzymes which effect the conversion of glucose to fructose are called glucose isomerases and are formed from such bacteria belonging, inter alia, to the genus Arthrobacter and the genus Actinoplanes. These enzymes are water soluble, and if they are merely added to aqueous solutions of glucose, recovery of enzyme for reuse is difficult and expensive. Using the enzyme only once also affords a process which is relatively expensive. Consequently, many techniques have been developed for immobilizing the enzyme in such a way that substantial enzymatic activity in isomerizing glucose to fructose is displayed while the enzyme itself remains rigidly attached to some water-insoluble support, thereby permitting reuse of the enzyme over substantial periods of time and for substantial amounts of glucose-containing solutions. One illustration of a method for immobilizing an enzyme is found in Levy and Fusee, U.S. Pat. No. 4,141,857, where a polyamine is adsorbed on a metal oxide such as alumina, treated with an excess of bifunctional reagent, such as glutaraldehyde, so as to cross-link the amine, thereby entrapping the resulting polymer in the pores of the metal oxide, and the contacting the mass with enzyme to form covalent bonds between the pendant aldehyde groups and an amino group on the enzyme. It is highly desirable that the material used in making immobilized enzyme contain the desired enzyme, here glucose isomerase, as chemically pure as possible, both to assure maximum loading on the support, and to assure that the immobilized enzyme product will be homogeneous in the kind of enzyme bound to the support, thereby insuring maximum specificity in the conversion of glucose to fructose.

SUMMARY OF THE INVENTION

A principal object of the invention is to provide a method of purifying and recovering glucose isomerase. In one embodiment the invention comprises removing nucleic acid from a solution containing glucose isomerase, subjecting said solution to chromatography in the presence of a cellulosic material, eluting the enzyme with a buffer solution, and recovering the resultant purified glucose isomerase. A specific embodiment comprises treating an enzyme-containing solution with a reagent, such as protamine sulfate, which precipitates nuclei acids, separating and discarding the solids, chromatographing the solution on a column of diethylaminoethyl cellulose, eluting the enzyme with an imidazole buffer containing potassium chloride and recovering the resultant purified glucose isomerase. A more specific embodiment comprises the application of this process to glucose isomerase which has been produced during the growth of a micro-organism from the genera Actinoplanes and Streptomyces on a culture medium.

Other objects and embodiments will be apparent from the following detailed description of this invention.

DESCRIPTION OF THE INVENTION

Enzymes with glucose isomerase activity are produced by many micro-organisms, including those of the genus Streptomyces, Lactobacillus, Curtobacterium, and Actinoplanes. Examples of particular species of glucose isomerase producers from the above genera include: A. missouriensis, A. philippenensis, A. armeniacus, L. pentosus, L. breves, C. citreum, C. luteum, C. helvolum, etc. The Streptomyces are particularly rich in glucose isomerase producers, and examples of such species include olivochromogenes, venezuelae, coelicolor, aureus, griseolus, and virginiae. By way of illustration only, A. missouriensis may be cultured on a medium containing a suitable carbon source and other appropriate nutrients for a time sufficient to give maximum, or near maximum, glucose isomerase activity. The whole cells containing the enzymes are collected by suitable means, such as filtration, washed, and resuspended in a buffer such as that provided for by imidazole at a pH from about 6 to about 8, which preferably contains magnesium ions at a concentration from about $10^{-3}$ to about $10^{-1}$ molar, and divalent cobalt ions at a concentration from about $10^{-4}$ to about $10^{-2}$ molar. If the cells are not to be utilized immediately they may be frozen and stored in that state until used.

The cells so produced contain much proteinaceous matter other than the desired glucose isomerase, and it is convenient to separate some of these by heat denaturation prior to entering the purification process. Such heat treatment may be omitted, however, but not necessarily with equivalent results. In one embodiment a suspension of cells such as that described above may be heated at about 60° C. for about 10 minutes to accomplish such denaturation. To release glucose isomerase from the whole cells the cell walls must be ruptured. Examples of suitable means which may be utilized to effect the cell wall rupture include either chemical rupture such as by digestion with a lysozyme enzyme preparation, or physical rupture such as by rendering the walls with sound waves (sonication) or mechanical grinding. In one embodiment the enzyme may be released by sonication at a temperature between about 0° C. and about 15° C., the cell debris which is formed then being removed by any means known to those skilled in the art, as, for example, by centrifugation.

The solution which is obtained thereby is composed of all of the contents of the cell, and includes glucose isomerase, other proteins not denatured by a heat treatment, if used, and nucleic acids. The nucleic acids can be selectively removed by addition of reagents which cause their precipitation. In a preferred embodiment of the invention the reagent which is utilized to effect this removal is selected from the group consisting of protamine, streptomycin, and their water-soluble salts, such as their sulfates. It is also contemplated within the scope of this invention that other salts, such as the nitrates, acetates, halides, and the like may also be used, but not necessarily with equivalent results. This reagent is added to the solution at a concentration from about 0.001 to about 1.0 weight-volume percent and preferably at a concentration from about 0.01 to about 0.1 weight-volume percent. After allowing precipitation of the solids to occur for a period of time which may range from about 20 to about 40 minutes, the solids are removed by suitable means, such as centrifugation, to provide a solution which is essentially free from nucleic acids.

Following the removal of the nucleic acids, the next step in the purification process is to separate glucose isomerase from most of the other proteinaceous material by chromatography. The solution obtained after removal of nucleic acids is applied directly to a chromatographic column packed with a cellulosic material. In a preferred embodiment the chromatographic medium is diethylaminoethyl cellulose, DEAE-cellulose. It is also contemplated that the use of other cellulosic materials such as triethylaminoethyl cellulose, polyacrylamide DEAE-cellulose, and the like, is within the scope of the invention, but not necessarily with equivalent results. After application of the enzyme-containing solution to the column, it is washed onto the column by a solution of the buffer in which the enzyme was dissolved, which buffer solution may also contain a salt dissolved therein. In a preferred embodiment this salt is selected from the group consisting of potassium chloride, sodium chloride, and lithium chloride at a concentration from about 0.05 to about 1.0 molar. Thereafter the enzyme is eluted from the cellulosic column by washing with a series of solutions of the aforementioned salts in the given concentration range dissolved in a solution of buffer, and those fractions showing highest enzyme activity are collected and combined.

The salts which are inherently present in the solution may be removed from the aforementioned combined fractions by any means known in the art, such as dialysis against a solution of 30-60% glucose dissolved in a solution of the same buffer used for solution of the enzyme. The glucose which is present is thereafter removed by further dialysis against 0.1 molar phosphate buffer at pH 7.0. By utilizing the process of this invention as hereinbefore described it is possible to obtain a purification of the enzyme up to about 11-fold, the purification being defined in that the specific activity, expressed in units of activity per milligram of protein, is about 11-fold greater for the final enzyme preparation than it was for the initial enzyme preparation. In addition, total recoveries of glucose isomerase enzyme range up to about 70%. By this is meant that the total activity of the final enzyme preparation is 70% of that of the initial enzyme preparation.

The enzyme which has been purified by the process described herein is eminently suitable for immobilization on an appropriate support. However, if a still further purified preparation is desired, this can be conveniently effected by chromatographing the purified enzyme preparation on a gel-like medium, such as polyacrylamide gel, or Sephadex (a trade name for a preparation sold by Pharmacia Co., which is hydrophilic, insoluble molecular sieve chromatographic medium made by cross-linking dextran) and the like. In a preferred embodiment of the invention, the chromatographic medium comprises Sephadex. The elution solvent which is employed to recover the enzyme in a step subsequent to the chromatography may be the same as that used for cellulosic chromatography. Again, the fractions which possess the highest glucose isomerase activity are combined to afford said enzyme with a purification in excess of 20-fold and at recoveries of about 90%.

The following examples illustrate the process described in this invention. These examples are merely illustrative and it is to be understood that the present invention is not necessarily limited thereto.

EXAMPLE 1

Glucose isomerase activity was assayed by a method based on the measurement of the initial rate of glucose formation from fructose, as opposed to the more conventional method based on the measurement of the initial rate of fructose formation from glucose. A 1.0 ml portion of appropriately diluted enzyme or enzyme-containing cells was mixed with an assay solution which contains fructose, 2.5 molar, tris(hydroxymethylamino)-methane hydrochloride buffer, $2 \times 10^{-2}$ molar at pH 7.5, magnesium sulfate, $5 \times 10^{-3}$ molar, and cobaltous chloride, $5 \times 10^{-4}$ molar. After incubation at 60° C. for 30-60 minutes, the reaction was terminated by addition of 1 ml of 0.1 N hydrochloric acid, and the formed glucose was measured by a glucose analyzer. One unit of glucose isomerase activity corresponds to the formation of 1 micromole glucose per minute, specific activity being defined as the number of micromoles of glucose formed per minute per milligram of protein.

Actinoplanes missouriensis (NRRL-B-3342) was cultured aerobically under forced air at 29° C. for 96 hours on a medium composed of corn steep liquor (2%), casein enzyme hydrolysate (2%), NaNO$_3$ (0.15%), MgSO$_4$ ($3 \times 10^{-3}$ M), CoCl$_2$ ($1 \times 10^{-4}$ M), glucose (0.2%), and phosphate buffer ($2.5 \times 10^{-2}$ M) at a pH of 7.1. The cells were harvested by filtration and washed twice with water to give 43 g. wet weight. A bacterial homogenate was prepared from a suspension of these cells in a buffer at pH 7.0 of 0.02 M imidazole containing $10^{-2}$ M MgSO$_4$ and $10^{-3}$ M CoCl$_2$, the homogenate being heated for 10 minutes at 60° C., thereafter chilled by immersion in ice, then sonified at temperatures under 10° C. Following this, the cell debris and heat-precipitated proteins were removed by centrifugation at 12,000 g for 20 minutes.

The nucleic acids which were present in the solution were then precipitated by the addition, with stirring, of a 1% solution of protamine sulfate in an amount of 6 ml. protamine sulfate solution per 100 ml. of enzyme solution. After 30 minutes the solids which formed were removed by centrifugation at 12,000 g. This clear supernatant liquid was applied to a DEAE-cellulose column ($2.5 \times 15$ cm), which had earlier been equilibrated with the aforementioned buffer solution, and after the adsorption the liquid was washed onto the column with the same buffer solution containing KCl, 0.2 M. The enzyme then was eluted with a buffer solution containing KCl at a higher concentration (0.4 M) using a flow rate of 60 ml. per hour. Several fractions of 12 ml. each were collected and the 16 fractions with the highest glucose isomerase activity were combined. The enzyme fractions were concentrated, first by dialysis overnight against a solution of 50% glucose in the aforementioned imidazole buffer, followed by dialysis against a 0.1 M phosphate buffer, pH 7.0.

A portion of purified enzyme corresponding to 1200 units of glucose isomerase activity was chromatographed on a $2.5 \times 53$ cm. Sephadex G-150 column. Fractions of 3.1 ml each were collected at a flow rate of 12 ml. per hour, and the five fractions of highest specific activity were pooled. After concentration by dialysis as described above, the preparation was subjected to disc electrophoresis. Only two minor bands, accounting for 10% or less of the protein, were observed. Hence the enzyme preparation was over 90% pure.

The results of the purification are summarized in the table below.

| Purification of Glucose Isomerase | | | | | |
|---|---|---|---|---|---|
| Total Activity (units) | | Overall Recovery, % | Specific Activity (Units/mg Protein) | | Degree of Purification |
| Initial | Final | | Initial | Final | |
| No Sephadex | | | | | |
| 8006 | 5360 | 67 | 1.2 | 13.7 | 11.4 |
| With Sephadex | | | | | |
| 1200 | 1060 | 59 | | 23.2 | 19.3 |

Comparison of the specific activity of the final enzyme preparation with the specific activity of the initial enzyme preparation shows about an 11-fold purification was obtained using DEAE-cellulose alone. Subsequent chromatography on Sephadex resulted in obtaining enzyme preparation with about a 20-fold purification. Comparison of the total activity of the final enzyme preparation with that of the initial enzyme preparation showed that the process of this invention affords a total receovery of about 70% of said glucose isomerase before the optional Sephadex chromatography, and about 60% after the Sephadex chromatography.

EXAMPLE 2

The experimental conditions utilized in this example were similar to those of Example 1. However, the amounts of reagents, enzymes, etc., in this experiment represented a significant scale-up in the amounts which were utilized in the experiment. Actinoplanes missouriensis was grown at 30° C. for 96 hours in 14 liters of the culture medium through which air was bubbled at 7 liters per minute to give, after filtration of the cells, denaturation of protein and sonication, $35 \times 10^3$ units of glucose isomerase activity. Subsequent purification followed the procedure described in Example 1, the results of which are summarized in the following table.

| Purification of Glucose Isomerase | | | | | |
|---|---|---|---|---|---|
| Total Activity (units) | | Overall Recovery, % | Specific Activity (Units/mg Protein) | | Degree of Purification |
| Initial | Final | | Initial | Final | |
| $35 \times 10^3$ | $28 \times 10^3$ | 80 | 1.2 | 12.8 | 10.7 |

As found in Example 1, the final enzyme preparation shows about an 11-fold purification. Comparison of the total activity of the final enzyme preparation with that of the initial enzyme preparation shows a total recovery of 80%, surpassing that of Example 1.

We claim as our invention:

1. A process for purifying an enzyme possessing glucose isomerase activity contained within a buffered solution of said enzyme which comprises the steps of:
    (a) treating said buffered solution of said enzyme with a nucleic acid precipitation reagent consisting essentially of a reagent selected from the group of streptomycin and water-soluble salts of said streptomycin in a concentration of from about 0.001 to about 1.0 weight-volume percent to precipitate essentially all of the nucleic acids from said buffered solution of said enzyme as a solid and to provide an enzyme solution essentially free of said nucleic acids;
    (b) passing said essentially nucleic acid free solution of said enzyme to a chromatographic column possessing chromatographic column packing to remove proteinaceous material from said solution of said enzyme by means of said chromatographic column packing comprising diethylaminoethyl cellulose; and
    (c) eluting said enzyme of said solution through said chromatographic packing of step (b) with said buffer of step (a) to produce purified enzymes possessing glucose isomerase activity.

2. The process of claim 1 wherein said enzyme having glucose isomerase activity is produced during the growth of a microorganism selected from the group consisting of the genera Actinoplanes, Streptomyces, and Lactobacillus on a culture medium.

3. The process of claim 2 wherein said microorganisms of the genus Actinoplanes are species selected from the group consisting of missouriensis, philippinensis, and armeniacus.

4. The process of claim 2 wherein said microorganisms of the genus Streptomyces are species selected from the group consisting of olivochromogenes, venezuelae, coelicolor, aureus, griseolus, and virginae.

5. The process of claim 1 wherein said water-soluble salt of streptomycin is streptomycin sulfate.

6. The process of claim 1 wherein said buffer is selected from the group consisting of imidazole, phosphate, and tris(hydroxymethylamino)methane.

7. The process of claim 1 wherein said buffer contains a salt selected from the group consisting of sodium chloride, potassium chloride and lithium chloride at a concentration from about 0.05 to about 1.0 molar.

8. The process of claim 1 wherein said enzyme is further purified by chromatography on a hydrophilic, molecular sieve medium.

* * * * *